(12) United States Patent
Brocwell

(10) Patent No.: US 12,193,747 B2
(45) Date of Patent: Jan. 14, 2025

(54) SELFIE CARE

(71) Applicant: Now Optics Intellectual Property, Palm Springs, FL (US)

(72) Inventor: Christopher B. Brocwell, Waynesville, OH (US)

(73) Assignee: Now Optics Intellectual Property, Palm Springs, FL (US)

( * ) Notice: Subject to any disclaimer, the term of this patent is extended or adjusted under 35 U.S.C. 154(b) by 956 days.

(21) Appl. No.: 17/204,918

(22) Filed: Mar. 17, 2021

(65) Prior Publication Data

US 2022/0296098 A1    Sep. 22, 2022

(51) Int. Cl.
*A61B 3/14* (2006.01)
*A61B 5/00* (2006.01)
*G16H 30/20* (2018.01)
*G16H 50/20* (2018.01)

(52) U.S. Cl.
CPC .............. *A61B 3/14* (2013.01); *A61B 5/6898* (2013.01); *A61B 5/742* (2013.01); *A61B 5/746* (2013.01); *G16H 30/20* (2018.01); *G16H 50/20* (2018.01); *A61B 2560/02* (2013.01)

(58) Field of Classification Search
CPC ..... A61B 3/0033; A61B 3/0041; A61B 3/111; A61B 3/14; A61B 5/0077; A61B 5/6898; A61B 5/7275; A61B 5/742; A61B 5/746; A61B 2560/02; G16H 30/20; G16H 30/40; G16H 40/63; G16H 50/20
See application file for complete search history.

*Primary Examiner* — Jack Dinh
(74) *Attorney, Agent, or Firm* — Shutts & Bowen, LLP

(57) ABSTRACT

Embodiments of the present invention provide a novel and non-obvious method, system and computer program product for the selfie image sourced diagnosis of prospective eye disease. In an embodiment of the invention, a method for diagnosing prospective eye disease includes acquiring a selfie image with a portable communications device, recognizing a portion of the selfie image as an eye and comparing the portion of the selfie image to a pre-stored image of the eye in order to detect a threshold change from the pre-stored image to the selfie image. Thereafter, in response to detecting the threshold change, an alert is displayed in a display of the portable communications device. In this regard, optionally, the threshold change can be classified, and the classification correlated to a prospective ophthalmological diagnosis through the use of a classification table. Then, the prospective ophthalmological diagnosis can be included in the alert.

3 Claims, 2 Drawing Sheets

SELFIE CARE

BACKGROUND OF THE INVENTION

Field of the Invention

The present invention relates to the field of optics and more particular to optometry and ophthalmological examination processes, systems and devices.

Description of the Related Art

The eye, as a distinguishing feature of the human face, is a complex organ both in its function and its prospective malfunction. As its primary function, the eye senses light and provides an electrical signal to the brain for processing into imagery. As a light sensitive organ, the eye requires several structurally supporting elements including a lubrication element, a debris shield, a lens and the sensors themselves. The complexity of the organ, thus, gives rise to many possible ailments. Like many other human organs of the anatomy, some malfunctions are readily observable with the trained eye, while others require specialized diagnostic equipment. However, unlike other human organs, some prospective disease or disorder can be visibly present, but unnoticed owing to the multiple layers of structure between the surface of the eye and the deepest interior portion of the eye, some of which may be visible to the observer without the benefit of specialized diagnostic equipment.

In this regard, it is common practice in the conduct of an eye examination to combine both a visual inspection of each eye, unaided by mechanically assistive devices with one or more machine assisted tests. For some of the mechanically assisted tests, dilation of the pupil is required, but for some informative tests, no dilation of the pupil is required. Thus, one might conclude any person could self-exam in order to detect an early warning of some eye disease. Yet so many changes of the eye are subtle and not detectible at first glance by an untrained eye. However, it can be these subtle changes that are cause to investigate more deeply using machine assisted techniques. Because most individuals do not recognize such subtle changes, in many instances the opportunity for the early detection of eye disease is lost pending a routine visit with a health care professional specializing in the diagnosis of eye disease.

BRIEF SUMMARY OF THE INVENTION

Embodiments of the present invention address deficiencies of the art in respect to diagnosing prospective eye disease and provide a novel and non-obvious method, system and computer program product for the selfie image sourced diagnosis of prospective eye disease. In an embodiment of the invention, a method for diagnosing prospective eye disease includes acquiring a selfie image with a portable communications device, recognizing a portion of the selfie image as an eye and comparing the portion of the selfie image to a pre-stored image of the eye in order to detect a threshold change from the pre-stored image to the selfie image. Thereafter, in response to detecting the threshold change, an alert is displayed in a display of the portable communications device. In this regard, optionally, the threshold change can be classified, and the classification correlated to a prospective ophthalmological diagnosis through the use of a classification table. Then, the prospective ophthalmological diagnosis can be included in the alert.

In one aspect of the embodiment, the threshold change is a threshold change in color of a collection of pixels of the selfie-image associated with a specific structural portion of the eye. In another aspect of the embodiment, the threshold change is a threshold change in a number of pixels accounting for a specific structural portion of the eye and in response to detecting the threshold change, the alert can be transmitted by electronic mail from the smart phone to a registered eyecare provider. In this regard, the alert can include both a portion of the selfie-image, optionally enhanced and magnified to show the changed pixels and surrounding pixels, and also counterpart portion of the pre-stored image.

In yet another aspect of the embodiment, the portable communications device is a smart phone with a touch screen display and dual camera lens, a first of the lenses positioned on an opposite side of the smart phone as the touch screen display, and a second of the lenses positioned at a same side of the smart phone as the touch screen display. As such, the acquisition of the selfie image includes detecting an acquisition of the image by one of the lenses of the smart phone, determining which of lenses had been used to acquire the image and, on the condition that it is determined that the second of the lenses positioned at the same side of the smart phone as the touch screen display acquired the image, identifying in the acquired image a face, matching the image of the identified face to a pre-stored image of a known face associated with the pre-stored image of the eye. The, on the condition that the identified face matches the known face, it may then be determined that the acquired image is the selfie image.

In another embodiment of the invention, a data processing system is adapted to diagnose prospective eye disease. The system includes a portable communications device having cellular communications circuitry, one or more processors, memory, a touch screen display, and a digital camera. The system also includes a selfie care module. The module in turn includes computer program instructions enabled while executing in the memory of the portable communications device to acquire a selfie image with the portable communications device, recognize a portion of the selfie image as an eye, compare the portion of the selfie image to a pre-stored image of the eye in order to detect a threshold change from the pre-stored image to the selfie image, and in response to detecting the threshold change, display an alert in the display of the portable communications device.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for the diagnosis of prospective eye disease utilizing self-acquired imagery. In accordance with an embodiment of the invention, an image captured by a smart phone can be determined to be a selfie image upon detecting a face of a person matching a face known to be that of the operator of the smart phone. Upon determining that captured imagery in the smart phone is a selfie image of an end user, an eye portion of the face of the person within the selfie image can be extracted and compared to a pre-stored image of the eye for the person. To the extent that a threshold difference in a designated set of pixels for a corresponding structural portion of the eye is detected, an alert can be displayed in a display of the smart phone. In this way, whenever a selfie image of the person is acquired, an opportunity for early detection of eye disease can be capitalized upon even though the person otherwise would not notice any observable changes in the eye.

Figure 1:
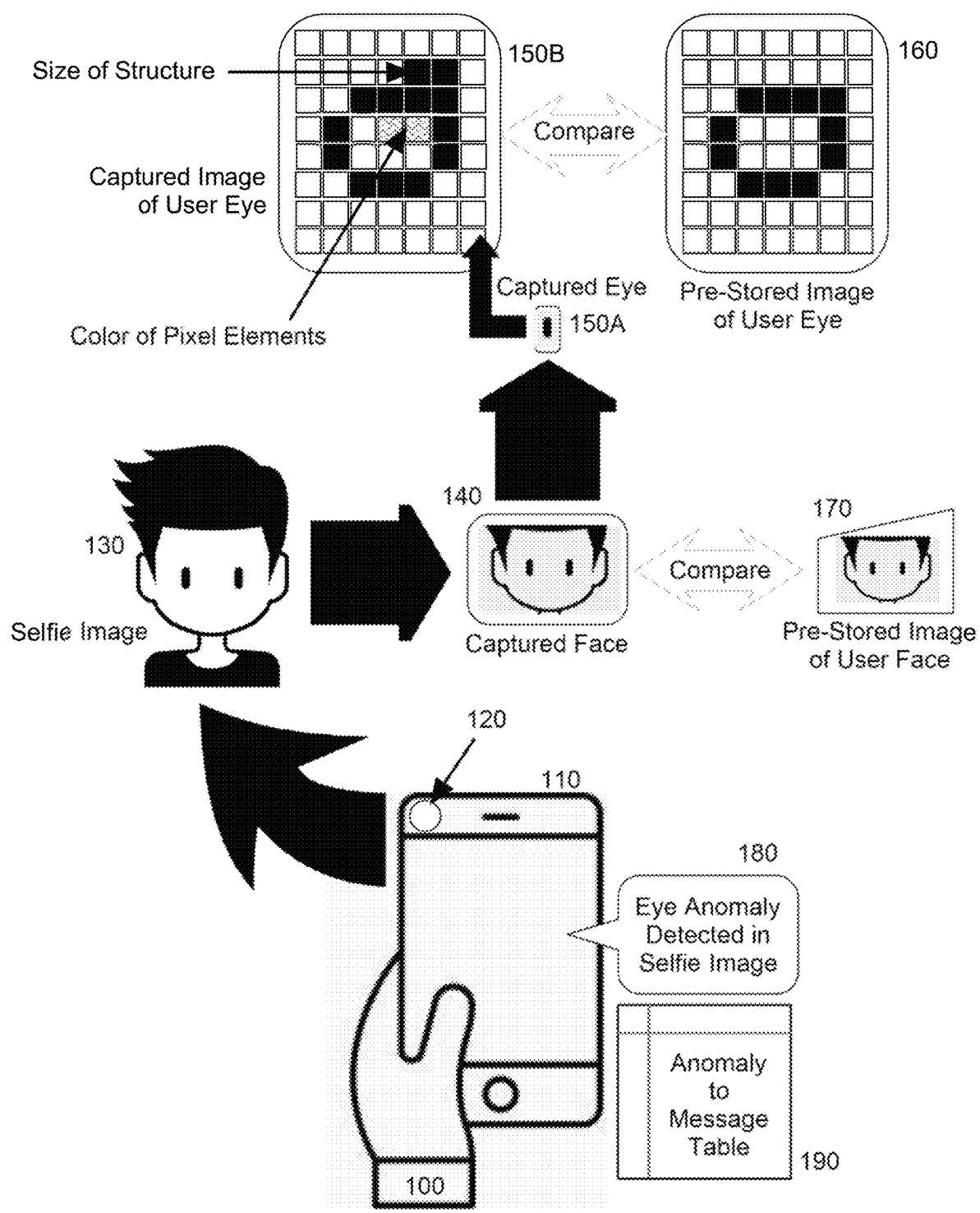
FIG. 1 is pictorial illustration of a process for the diagnosis of prospective eye disease using self-acquired imagery.

In further illustration, FIG. 1 pictorially shows a process for the diagnosis of prospective eye disease using self-acquired imagery. As shown in FIG. 1, an end user 100 directs a smart phone 110 to capture an image 130 using front facing camera 120 of the smart phone 110. An image of a face 140 is extracted from the captured image 130 and then compared to a pre-stored image 170 of the face of the end user 100. To the extent that the extracted image of the face 140 matches the pre-stored image of the user face 170, it is then determined that the captured image 130 is a selfie image. As such, an eye portion 150A is located within the captured image 130 and extracted for analysis.

Specifically, a pixel map 150B of the eye portion 150A is then compared to a pre-stored pixel map 160 of the eye of the end user 100. In this regard, first the pixel map 150B is aligned with the pre-stored pixel map 160 so that the location and orientation of the eye represented in the pixel map 150B correlates with the location and orientation of the eye represented in the pre-stored pixel map 160. Then, one or more portions of the pixel maps 150B, 160 are compared to one another to determine a threshold difference, for example a difference in color of the structure of the eye as represented in the pixel maps 150B, 160, or a difference in size of the structure of the eye as represented in the pixel maps 150B, 160.

To the extent that one or more clusters of pixels in the pixel maps 150B, 160 differ from one another by a threshold amount, it is concluded that the state of the eye of the end user 100 has changed since the time when the pre-stored pixel map 160 was acquired. Consequently, the nature of the difference, represented for instance as a vector of pixel value differences, can be matched to a record in a table of anomalies 190 in order to retrieve a specific message, such as an indication of possible eye condition. Thereafter, the specific message is included in an alert 180 presented in a display of the smart phone 110.

Figure 2:
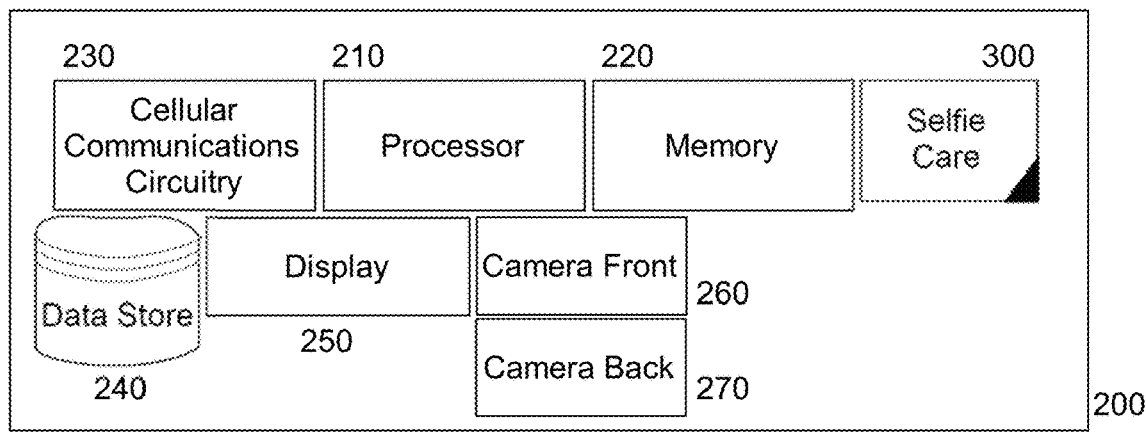
FIG. 2 is a schematic diagram of a data processing system adapted for diagnosing prospective eye disease using self-acquired imagery; and, FIG. 3 is a flow chart illustrating a process for diagnosing prospective eye disease using self-acquired imagery.

The process shown in FIG. 1 can be implemented within a data processing system. In further illustration, FIG. 2 schematically shows a data processing system adapted for diagnosing prospective eye disease using self-acquired imagery. The system can include a smart phone 200 having one or more processors 210, memory 220, cellular communications circuitry 230, fixed storage 240 and a display 250. As well, the smart phone 200 includes at least two cameras 260, 270—a front facing camera adjacent to the display 250 and a rear facing camera 270 on an opposite side of the smart phone 200 from the display 250. Of note, a selfie care module 300 executes in the memory 220 by the one or more processors 210 of the smart phone 200.

In this regard, the selfie care module 300 includes computer program instructions that during execution in the memory 220, are operable to detect when an image has been captured by the front facing camera 260 and whether or not the captured image is a selfie of the end user associated with the smart phone 200. The program instructions are further operable to extract from the selfie image, a pixel map of an eye portion and to compare the pixel map to a pre-stored pixel map of the same eye portion of the end user. To the extent that a threshold difference is detected between the maps, the program instructions characterize the threshold difference and lookup a corresponding message for the characterization. Finally, the program instructions include the message in an alert displayed in the display 250.

Figure 3:
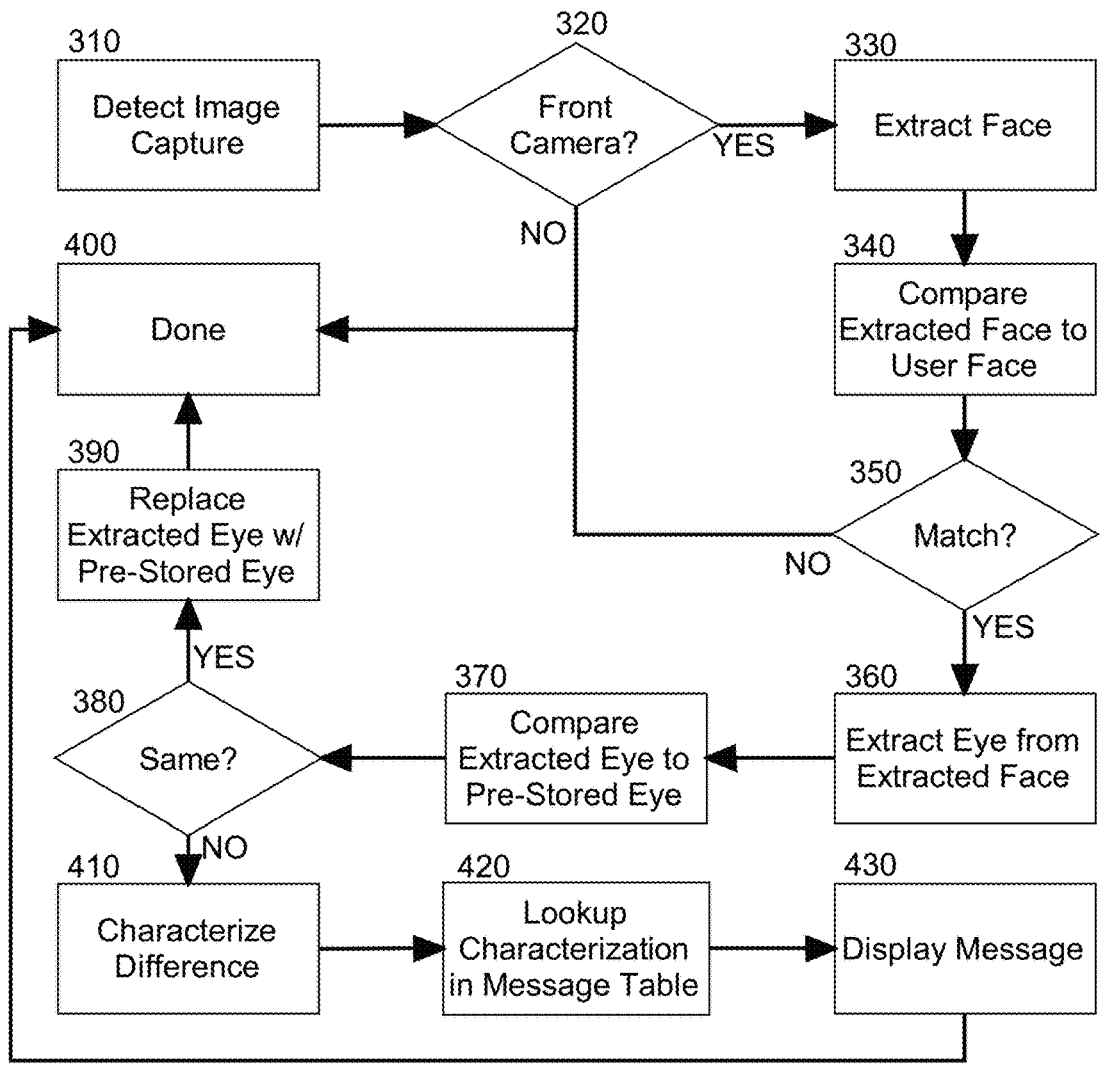

In even further illustration of the operation of the selfie care module 300, FIG. 3 is a flow chart illustrating a process for diagnosing prospective eye disease using self-acquired imagery. Beginning in block 310, an image capture event is detected in the smart phone and in decision block 320, it is determined whether or not the image had been captured by the front facing camera thereby indicating the possibility of a selfie image. If so, in block 330, a face is extracted from the captured image and compared, in block 340, to a pre-stored image of the end user. To the extent that the extracted image compares to the pre-stored image, it can be conclusively determined that the captured image is a selfie image.

Consequently, in block 360, an eye portion of the face is extracted into a pixel map and compared in block 370 to a pre-stored pixel map of the eye of the end user. Then, in decision block 380, if the pixel maps are determined to match within a threshold number of pixels, in block 390 the extracted pixel map is stored in the smart phone as a replacement to the pre-stored pixel map. But otherwise, in block 400, the differences in the pixels between the pre-stored pixel map and the extracted pixel map are characterized, for instance, by generating a vector of each pixel difference between the pixel maps. Thereafter, in block 420, a record is located in a table using the vector as a key so as to retrieve a specific message correlated to the vector. Finally, the retrieved message is display in block 430.

The present invention may be embodied within a system, a method, a computer program product or any combination thereof. The computer program product may include a non-transitory computer readable storage medium or media having computer readable program instructions stored thereon, which when executed within the computer, cause one or more processors to perform different processes exemplary of different aspects of the present invention. To that end, the non-transitory computer readable storage medium can be a tangible device that can retain and store instructions for use by an instruction execution device such as a processor (central processing unit or "CPU").

Aside from direct loading from memory for execution by one or more cores of a CPU or multiple CPUs, the computer readable program instructions described herein alternatively can be downloaded from over a computer communications network into the memory of a computer for execution therein. As well, only a portion of the program instructions may be retrieved into memory of the computing device from over a computer communications network, while other portions may be loaded from persistent storage of the computing device. Even further, only a portion of the program instructions may execute by one or more processing cores of one or more CPUs of the computing devices while other portions may cooperatively execute within a different computing device positioned remotely over the computer communications network with results of the computing by both devices shared therebetween.

Even yet further, as it is to be understood, one or more aspects of the present invention have been described herein with reference to flowchart illustrations and/or block diagrams of methods, apparatus (data processing systems), and computer program products according to embodiments of the invention. It will be understood that each block of the flowchart illustrations and/or block diagrams, and combinations of blocks in the flowchart illustrations and/or block diagrams, can be implemented by computer readable program instructions in various combinations. These computer readable program instructions may be provided to a CPU of a general-purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function or functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "include", "includes", and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

I claim:

1. A data processing system adapted to diagnose prospective eye disease, the system comprising:
    a portable communications device comprising cellular communications circuitry, one or more processors, memory, a touch screen display, and a digital camera; and,
    a selfie care module comprising computer program instructions enabled while executing in the memory of the portable communications device to perform:
    acquiring a selfie image with the portable communications device;
    recognizing a portion of the selfie image as an eye;
    comparing the portion of the selfie image to a pre-stored image of the eye in order to detect a threshold change from the pre-stored image to the selfie image;
    responsive to detecting the threshold change, displaying an alert in the display of the portable communications device;
    classifying the threshold change;
    looking up a prospective ophthalmological diagnosis corresponding to a classification in a classification table; and,
    including the prospective ophthalmological diagnosis in the alert;
    wherein the portable communications device is a smart phone with a touch screen display and dual camera lens, a first of the lenses positioned on an opposite side of the smart phone as the touch screen display, and a second of the lenses positioned at a same side of the smart phone as the touch screen display, the acquisition of the selfie image comprising:
    detecting an acquisition of the image by one of the lenses of the smart phone;
    determining which of lenses had been used to acquire the image; and, on condition that it is determined that the second of the lenses positioned at the same side of the smart phone as the touch screen display acquired the image, identifying in the acquired image a face, matching the image of the identified face to a pre-stored image of a known face associated with the pre-stored image of the eye, and on condition that the identified face matches the known face, determining that the acquired image is the selfie image.

2. The system of claim 1, wherein the threshold change is a threshold change in color of a collection of pixels of the selfie-image associated with a specific structural portion of the eye.

3. The system of claim 1, wherein the threshold change is a threshold change in a number of pixels accounting for a specific structural portion of the eye.

* * * * *